United States Patent
Mowrey-McKee et al.

(10) Patent No.: US 7,419,944 B2
(45) Date of Patent: Sep. 2, 2008

(54) AQUEOUS DISINFECTING SYSTEMS

(75) Inventors: Mary Mowrey-McKee, Alpharetta, GA (US); Marc Ajello, Decatur, GA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/997,099

(22) Filed: Nov. 29, 2001

(65) Prior Publication Data

US 2002/0122831 A1   Sep. 5, 2002

Related U.S. Application Data

(60) Provisional application No. 60/253,757, filed on Nov. 29, 2000.

(51) Int. Cl.
    *C11D 3/00*   (2006.01)
(52) U.S. Cl. .................... 510/112; 514/839; 514/840
(58) Field of Classification Search ............... 514/642, 514/912, 25, 112, 115, 839, 840; 424/401; 510/112
    See application file for complete search history.

(56) References Cited

U.S. PATENT DOCUMENTS

| | | | |
|---|---|---|---|
| 4,758,595 A | 7/1988 | Ogunbiyi et al. | ............ 514/635 |
| 5,312,749 A | 5/1994 | Griffin et al. | ................ 435/220 |
| 5,422,073 A | 6/1995 | Mowrey-McKee et al. | .... 422/28 |
| 5,474,700 A * | 12/1995 | Griffin et al. | ........... 252/174.12 |
| 5,500,186 A | 3/1996 | Mowrey-McKee et al. | .... 422/28 |
| 5,593,637 A | 1/1997 | Mowrey-McKee et al. | .... 422/28 |
| 5,817,277 A | 10/1998 | Mowrey-McKee et al. | .... 422/28 |
| 6,121,327 A * | 9/2000 | Tsuzuki et al. | ............. 514/642 |
| 6,162,393 A * | 12/2000 | De Bruiju et al. | ............ 422/28 |
| 6,417,144 B2 * | 7/2002 | Tsuzuki et al. | |
| 7,067,547 B1 * | 6/2006 | Smith | ........................ 514/396 |

FOREIGN PATENT DOCUMENTS

| | | |
|---|---|---|
| GB | 1 432 345 | 4/1976 |
| WO | WO 92/11878 | 7/1992 |
| WO | WO 95/10605 | 4/1995 |
| WO | WO 02/38161 | 5/2002 |

OTHER PUBLICATIONS

International Search Report.

* cited by examiner

*Primary Examiner*—Gina C Yu
(74) *Attorney, Agent, or Firm*—Sheng-Hsin Hu; Robert J. Gorman

(57) ABSTRACT

Compositions effective as disinfecting solutions for ophthalmic devices such as contact lenses are provided. The compositions include a microbicide, preferably polyhexamethylene biguanide or alexidine, and a water soluble salt of a bis-aminopolyol, preferably 1,3-bis(tris[hydroxymethyl]methylamino)propane, as a buffering agent.

9 Claims, No Drawings

AQUEOUS DISINFECTING SYSTEMS

STATEMENT OF RELATED CASES

This application claims priority of application Ser. No. 60/253,757, filed Nov. 29, 2000.

This invention relates generally to aqueous solutions useful for disinfecting ophthalmic devices. More specifically, the invention pertains to solutions that utilize a specific type of buffer system acting in synergy with certain microbicides. Such solutions are particularly useful as a basis for formulating contact lens care products.

Disinfecting solutions for use in conjunction with contact lenses have been in use essentially for as long as contact lenses have been available to the public. U.S. Pat. No. 4,758,595 discloses a solution comprising a microbicidally or fungicidally effective amount of a polyhexamethylene biguanide (PHMB) or water-soluble salt thereof, in combination with a borate buffer system. It should be noted that this patent emphasizes the importance that the solutions specifically contain a borate buffer, since the borate buffered PHMB solutions evaluated were more effective then corresponding phosphate buffered solutions at the desired low PHMB concentrations. British Pat. 1,432,345 discloses contact lens disinfecting compositions containing a polymeric biguanide as the microbicide and a phosphate buffer. The concentration of the PHMB microbicide in the solutions disclosed in this patent is substantially higher than the PHMB concentrations of the present invention.

While biological buffers based on 1,3-bis(tris[hydroxymethyl]methylamino)propane are well known, the application of these buffers in lens care solutions is not common. U.S. Pat. No. 5,474,700 discloses a novel alkaline protease derived from ship worm bacterium which is taught as being useful in contact lens cleaning solutions. It is further disclosed that such solutions may additionally contain various detergents, surfactants, buffers, stabilizers and the like. In this patent the inhibition of protease activity was measured in a 1,3-bis(tris[hydroxymethyl]methylamino)propane buffered solution. However, this patent does not teach or suggest the inclusion of 1,3-bis(tris[hydroxymethyl]methylamino)propane in ophthalmic solutions, but teaches only the use of this buffer system in performing the enzymatic assays.

There is considerable diversity in the makeup of the various formulations used as contact lens care solutions, primarily due to the fact that to date no single solution has been found to meet all of the parameters desired for the various types of lenses. For example, some of the currently commercially available solutions offer low irritancy and/or hypersensitivity, but require a minimum of four (4) hours soaking to effectively disinfect. Other commercially available solutions contain microbicides such as thimerosol which has been particularly problematical as a disinfecting agent, and there has been a general attempt to avoid use of thimerosol as an antimicrobial agent. Also, compositions containing borate buffer systems have been known to be irritating to the eyes of certain individuals.

A second, and not small consideration, is that of contact lens material/solution compatibility. Disinfection at elevated temperature is not a practical alternative for use with high water content soft contact lenses. Some lenses entrap or react with various components of certain disinfection solution making it impossible to utilize such solutions with those lenses. For this reason, proper patient compliance with lens/solution match-up directions is essential to maintaining contact lenses properly. Yet experience has shown that patient compliance with lens and solution manufacturer directions is not adhered to by a significant, although small patient population. Finally, not all disinfectant solutions are suitably effective against the entire range of microbial organisms which are of concern in the contact lens field. Hence, there have been efforts to develop disinfection solutions that are generally useful for most, if not all, contact lenses currently available.

Many of the previous efforts to alleviate the problem of binding and concentrating disinfectants and preservatives onto contact lens surfaces, and for reducing the potential for eye tissue irritation have not been totally satisfactory. For example, in spite of low toxicity levels not all disinfectants are compatible for use with all types of contact lenses.

Accordingly, there is a need for improved disinfecting solutions that are compatible for use with most types of contact lenses while maintaining both a high level of antibacterial activity and a low order of toxicity to eye tissue with little or no binding or concentrating of the disinfecting agent onto lens surfaces.

The present invention provides improved compositions for disinfecting ophthalmic devices such as such as hard (PMMA), soft (hydrophilic), and rigid gas permeable (RGP) contact lenses. These compositions allow for the formulation of disinfecting solutions with high efficacy at low microbicide concentrations. Furthermore, the general compatibility of the active components of the compositions of this invention with the common ophthalmologically acceptable additives used in such solutions allows presents a broad latitude in formulating solutions for ophthalmic uses.

The present invention is based upon the unexpected and beneficial finding that disinfecting solutions buffered with 1,3-bis(tris[hydroxymethyl]methylamino)propane and which also contain certain microbicides and fungicides exhibit a synergy resulting in a microcidal activity significantly higher than the activity of these same active ingredients used in conjunction with other buffers. A screening study was performed with 15 common biological buffers each employed independently in conjunction with the antimicrobial agents polyhexamethylene biguanide or alexidine, and it was observed that solutions containing 1,3-bis(tris[hydroxymethyl]methylamino)propane as the buffering agent exhibited antimicrobial activity which was significantly higher than that of comparable solutions employing any of the other buffering agents in the study.

The buffering agent 1,3-bis(tris[hydroxymethyl]methylamino)propane is a commercially available compound also known by the designations BIS-TRIS propane and BTP. It is a member of the general class of bis-aminopolyols compounds depicted by formula (I).

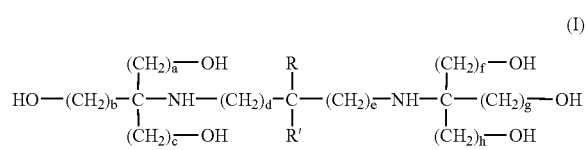

wherein a, b, c, d, e, f, g, and h are independently an integer from 1 to 6; and R and R' are independently chosen from the group consisting of —H, —$CH_3$, —$(CH_2)_{2-6}$—H, and —$(CH_2)_{1-6}$—OH;

Furthermore, in the present invention the buffering agents described by formula (I) may be provided in the form of various water-soluble salts.

BIS-TRIS propane is described under biological buffers in Biochemicals and Reagents, Sigma-Aldrich Co., 2000-2001 edition. The dissociation constants for this dibasic compound are $pKa_1=6.8$ and $pKa_2=9.5$ which renders aqueous solutions of this compound useful as a buffering agent in the pH range of about 6.3-9.3. The specific structure of 1,3-bis(tris[hydroxymethyl]methylamino)propane is shown in formula II.

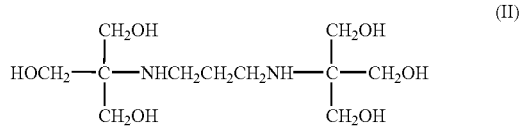

It is expected that many of the structural variations of BIS-TRIS propane indicated by formula (I) will exhibit activity similar to that of BIS-TRIS propane. All of the structural variations described by formula (I) maintain the dibasic nature of the molecule as well as the inductive electronic environment of the secondary amino nitrogen atoms. Therefore, it is expected that the dissociation constants of any of the compounds described by formula (I) will be about the same as the dissociation constants reported for BIS-TRIS propane provided that said compounds maintain the requisite aqueous solubility.

In one series of the variations of formula (I), wherein the variation of each of a, b, c, d, e, f, g, and h independently as an integer from 1 to 6 and wherein R and R' are independently chosen from the group consisting of H, $CH_3$, $(CH_2)_{2-6}$—H, the hydroxyl functionality, i.e. the number of hydroxyl moieties per molecule, is maintained. The hydroxyl functionality of 1,3-bis(tris[hydroxymethyl]methylamino)propane is 6. In another series of the variations of formula (I), wherein R and/or R' is $(CH_2)_{1-6}$—OH the total hydroxyl functionality is either 7 or 8. The increased hydroxyl functionality in the compounds affects properties such as aqueous solubility, hydrogen bonding potential, and surfactant activity without affecting buffering efficiency in the ophthalmologically acceptable range. It is recognized that the structural variations of formula (I) may be employed in any and all combinations. It is also recognized that various salts of any of the compound of formula (I) as well as mixtures of the compounds of formula (I) are useful for the purpose of providing the buffer systems of the present invention. Furthermore, specific structural variations designed to impart specific secondary properties and characteristics to the compounds of formula (I) while maintaining the essential buffering function will be apparent to those skilled in the art. Therefore, the examples of structural variation presented in this specification are for illustrative purposes and are not intended to in any way limit the scope of the invention.

As used in this specification and claims, the term "ophthalmologically acceptable" describes materials which are soluble in the solution at effective concentrations and which will neither harm nor irritate the tissue of the eye. Furthermore, these ingredients will not adversely affect the properties or utility of the device on which such solutions are used. This is particularly important in the case of soft contact lenses and rigid gas permeable contact lenses, since such lenses may absorb components of disinfecting and preserving solutions and such components may become concentrated to levels, such that when released, these components may cause corneal inflammation and other eye tissue irritation. Examples of ophthalmologically acceptable ingredients are given throughout the specification. Of course, the use of other ophthalmologically acceptable ingredients not described herein, as well as ingredients that may be come available in the future, is within the scope of this invention.

At the concentrations used in this invention 1,3-bis(tris[hydroxymethyl]methylamino)propane is harmless to the eye and to known contact lens materials and is, therefore, ophthalmologically acceptable. It is important that the pH of the solutions of the present invention be adjusted and maintained at an ocularly acceptable level to be compatible with both the environment of the eye and the contact lens. Typically this pH should be between 6.0 to 8.0, preferably between 6.7 to 7.7. Significant deviations from neutral (pH 7) of these compositions may cause changes in the physical parameters (i.e. diameter) in some contact lenses. Low pH (below 5.5) can cause burning and stinging of the eyes, while very low or very high pH (below 3.0 or greater than 10) can cause ocular damage.

The present invention provides a method and compositions for disinfecting contact lenses against a wide range of microorganisms including but not limited to *Fusarium solani, Staphylococcus aureus, Pseudomonas aeruginosa, Serratia marcescens* and *Candida albicans*. Furthermore, the present invention provides a method and compositions for disinfecting hard (PMMA) contact lenses and soft (hydrophilic) lenses as well as rigid gas permeable (RGP) contact lenses. A further advantage of the present invention is that it provides a method and compositions for disinfecting contact lenses with a low potential for irritating the eyes. A still further advantage of the present invention is that in certain embodiments, it provides a method and composition for disinfecting contact lenses, for cleaning tear film debris from contact lenses, and for lubricating contact lenses, and for preserving contact lenses. For the purposes of the present invention he term "disinfect" means the rendering non-viable of substantially all pathogenic microbes that are in the vegetative state, including gram negative and gram positive bacteria, as well as fungi. The chemical compounds and compositions that render such pathogenic microbes inactive are known as microbicides.

In its preferred aspects the present invention provides for improved solutions for disinfecting contact lenses. The solutions are compatible with both hard and soft type lenses, and are adaptable for use with virtually any of the commonly known disinfecting techniques, including "cold" soaking under ambient temperature conditions, as well as with high temperature disinfecting methods. The disinfecting solutions of the present invention are especially noteworthy for their wide spectrum of bactericidal and fungicidal activity at low concentrations coupled with very low toxicity and reduced affinity for binding and concentrating when used with soft type contact lenses.

The solutions of the present invention must contain a microbicide in a concentration sufficient to effect the desired disinfection of a contact lens. The specific concentrations required for the microbicides useful in this invention must be determined empirically for each microbicide. Some of the factors affecting the effective concentration are specific activity of the microbicide against the specified pathogens, the molecular weight of the microbicide, and the solubility of the microbicide. It is also important that the chosen microbicides be employed in a physiologically tolerable concentration. The list of microbicides which may be employed in the present invention include, but is not in limited to polyhexamethylene biguanide (PHMB), alexidine, hexetidine, chlorhexidine, N-alkyl-2-pyrrolidone, polyquaternium-1, bronopol, it benzalkonium chloride, and hydrogen peroxide.

Typical solutions of this invention contain the microbicides PHMB or alexidine in concentrations from about 0.01 to 10 ppm and 1,3-bis(tris[hydroxymethyl]methylamino)propane in a concentration from about 0.001 to 0.20 molar propane as the buffering agent. The acidity of the solution is then adjusted by the addition of either HCl or NaOH to a final pH of about 6.4-7.8 with the preferred range being 6.8-7.5.

Additionally, the disinfecting solutions may contain additional ingredients such as tonicity agents, chelating agents, surfactants, viscosity modifying agents, emollients, and demulcents, which may aid in either the lens cleaning or in providing lubrication to the eye.

Suitable occularly acceptable tonicity agents include, but are not limited to sodium chloride, potassium chloride, glycerol, mannitols, and mixtures thereof. The tonicity of the solution is typically adjusted to approximately 220 to 310 milliosmoles per kilogram solution (mOsm/kg) to render the solution compatible with ocular tissue and with hydrophilic contact lenses.

Suitable surfactants include, but are not limited to tyloxapol, which is 4-(1,1,3,3-tetramethylbutyl)phenol polymer with formaldehyde and oxirane; poloxamers (Pluronic™ and Pluronic-R™) which are nonionic surfactants consisting of block copolymers of propylene oxide and ethylene oxide; octoxynol or octyphenoxy polyethoxyethanol prepared by reacting isooctylphenol with ethylene oxide; poloxamine which is a block copolymer derivative of ethylene oxide and propylene oxide combined with ethylene diamine; and non-oxynol nonionic surfactant mixtures prepared by reacting nonylphenols with ethylene oxide. The surfactants can be employed in amounts ranging from about 0.0001 to about 20% by weight, preferably from about 0.005 to about 5.0% by weight, more preferably from about 0.025 to about 1.0% by weight. In one embodiment, 0.05% by weight of a polyoxypropylene-polyoxyethylene block copolymer (PLURONIC® F127) is used as a surfactant.

Suitable viscosity modifying agents include, but are not limited to lecithin or the cellulose derivatives such as hydroxymethylcellulose, hydroxypropylcellulose, hydroxypropylmethylcellulose, and methylcellulose in quantities similar to those used for the surfactants.

One embodiment of the present invention is an aqueous solution which includes at least one ophthalmologically acceptable microbicide and BIS-TRIS propane with a final solution pH of 6.7 to 7.5. The solution also includes an ophthalmologically acceptable tonicity agent, ophthalmologically acceptable chelating agent, an ophthalmologically acceptable surfactant, and an ophthalmologically acceptable viscosity modifying agent. Such a composition is especially useful for disinfecting ophthalmic devices such as contact lenses.

It should be emphasized here that the invention is also applicable beyond the field of ophthalmic device disinfection and preservation and may be used anywhere that a disinfecting solution treatment or a preserved solution would be useful, provided only that the material treated is not adversely affected by the composition components. For these purposes the compositions need not be ophthalmic device compatible or even pharmaceutically acceptable. The only important feature in such a case is that the solution contain 1,3-bis(tris[hydroxymethyl]methylamino)propane and at least one microbicide. Typical non-ophthalmic device disinfecting applications for which such compositions are useful include: lens case cleaner and disinfectant, topical medical composition, cosmetics, facial cleaner, hand cleaner, disinfecting soaps such as surgical soap, shampoo, household disinfectant, and industrial disinfectant, laboratory disinfectant, dental and medical equipment disinfectant, acne cleaning and disinfecting treatments, insect bite disinfection, for minor skin itching and rashes and wound healing applications. It is also suitable as a rapid in-office contact lens disinfecting/cleaning regimen.

The following examples are presented for illustrative purposes and are not intended to in any way limit the scope of this invention.

EXAMPLE 1

In this example common buffers plus approximately 1.2 ppm PHMB are evaluated for antimicrobial activity against *Candida albicans*. The pH and molarity of each solution was adjusted to approximately the same values. In that log reductions are estimated by visual observation of solution color and/or pellet formation in the bottom of the test tube, the test is semi-quantitative. All tests were performed in duplicate. All of the biological buffers shown in are described in Biochemicals and Reagents, Sigma-Aldrich CO., 2000-2001 edition Sigma-Aldrich, or online at URL sigma-aldrich.com.

Tubes of sterile solutions of buffer of equal molarity plus approxiamately 1.2 ppm PHMB are challenged with a suspension of Candida albicans at approx. $4 \times 10^5$ cfu/ml. Following 4.0 hour exposure, aliquots of each test solution are serially diluted to $10^{-5}$ in DEB. Following approx. 40 hours incubation at ~32° C., the tubes are observed for discoloration of the DEB and for a pellet in the $10^{-5}$ tube. The entire study is then performed in duplicate. Based on these observations, the estimated relative antimicrobial activity is assigned as shown In Table 1 below. Borate and BIS-TRIS propane show superior activity in this study. BIS-TRIS and TAPSO also exhibit better activity than phosphate ($PO_4$).

TABLE 1

| Buffer | log reduction |
|---|---|
| BIS-TRIS propane | 2-3 |
| Borate | 2-3 |
| BIS-TRIS | 1 |
| TAPSO | 1 |
| TES | <1 |
| PO4 | <1 |
| ACES | <1 |
| DIPSO | <1 |
| HEPES | <1 |
| MOBS | <1 |
| MOPS | NONE |
| MOPSO | NONE |
| ADA | NONE |
| BES | NONE |
| PIPES | NONE |

EXAMPLE 2

This example compares the efficacy of the microbicide alexidine in solutions utilizing a BIS-TRIS propane buffer compared to solutions utilizing a phosphate buffer. Sterile aqueous solutions are prepared at pH 7.3-7.7 according to the formulations shown in Table 2.

TABLE 2

| Formulation | A | B |
|---|---|---|
| Alexidine (ppm) | ~4 | ~4 |
| BIS-TRIS propane buffer (mol/L) | 0.1 | |
| Phosphate buffer (mol/L) | | 0.1 |
| EDTA[a] wt % | 0.025 | 0.025 |

TABLE 2-continued

| Formulation | A | B |
|---|---|---|
| Urea wt % | 0.03 | 0.03 |
| HEC[b] QP40 Wt % | 0.05 | 0.05 |

[a]EDTA* = ethylenediamine tetraacetic acid, disodium salt
[b]HEC** = hydroxyethyl cellulose The effectiveness of the solutions challenges with the microbe *Canida albicans* (ATCC No. 10231) is evaluated according to the USP XXI (51) Antimicrobial Preservative-Effectiveness Test. Results of this study are presented in Table 3.

TABLE 3

| Formulation | log reduction after 4 hr exposure to *Candida albicans* |
|---|---|
| A | 4.2 |
| B | 3.2 |

The antimicrobial activity data shown in Table 3 clearly show the enhanced effectiveness of the microbicide alexidine against *Candida albicans* in a solution buffered with BIS-TRIS propane (formulation A) compared to a similarly formulated solution buffered with a standard phosphate buffer (formulation B). The BIS-TRIS propane buffered formulation A shows a 1.0 log greater reduction than does the phosphate buffered formulation B.

EXAMPLE 3

This example compares the efficacy of disinfecting solutions utilizing TRIS-BIS propane buffer with solutions utilizing a standard phosphate buffer. Sterile solutions are prepared according to the formulations shown in Table 4. The control formulation utilizes a standard phosphate buffer while all other formulations utilize TRIS-BIS propane buffer. The final solutions are adjusted to a tonicity of 280-300 mOsmol/kg by the addition of NaCl and to a pH of 7.2-7.4 by the addition of either HCl or NaOH as required.

TABLE 4

| Ingredient | control | A | B | C | D | E | F |
|---|---|---|---|---|---|---|---|
| standard phosphate buffer | + | | | | | | |
| TRIS-BIS propane (0.1 M) | | + | + | + | + | + | + |
| PHMB (1 ppm) | + | + | + | + | + | + | + |
| EDTA (0.025% wt) | + | + | + | + | + | + | + |
| Pluronic F127[a] (0.05% wt) | + | + | + | | + | + | |
| Cremophor RH40[b] (0.1% wt) | | | + | + | | + | + |
| Urea (0.03% wt) | | | | | + | + | + |

[a]poloxamer, propylene oxide/ethylene oxide block copolymer
[b]non-ionic surfactant, derivative of castor oil and ethylene oxide Each of the formulations in Table 4 is tested according to procedure of ISO/FDIS 1.4729 (Ophthalmic optics—Contact lens care products). The log reductions after 4.0 hr exposure to *Candida albicans* is presented in Table 5.

TABLE 5

| | control | A | B | C | D | E | F |
|---|---|---|---|---|---|---|---|
| log reduction against C.a. | 0.3 | 3.8 | 3.6 | 3.3 | 3.9 | 4.0 | 3.7 |

The data presented in Table 5 clearly demonstrate that the formulations A, B, C, D, E and F, which utilize a TRIS-BIS propane buffer, significantly exceed log reductions for *Candida albicans* compared to a standard phosphate buffer control.

I claim:

1. An aqueous solution for disinfecting a contact lens, comprising: from 0.1 to 10 ppm of a microbicide selected from the group consisting of polyhexamethylene biguanide and alexidine; and 0.001 to 0.2 mol/L of 1,3-bis(tris[hydroxylmethyl]methylamino)propane or a salt thereof as buffering agent, wherein the aqueous solution buffered by 1,3-bis(tris[hydroxylmethyl]methylamino)propane is characterized by having a disinfecting efficacy that is at least 1.0 log of reduction greater than a disinfecting solution containing the same amount of the microbiocide but buffered with a phosphate buffer, wherein said solution has a pH of 6.8 to 7.5.

2. The aqueous solution of claim 1 further comprising a chelating agent.

3. The aqueous solution of claim 2 wherein said chelating agent is selected from the group consisting of ethylene diamine tetraacetic acid, diethylene triamine pentaacetic acid, salts thereof, and mixtures thereof.

4. The aqueous solution of claim 1 further comprising a surfactant.

5. The aqueous solution of claim 4 wherein said surfactant is selected from the group consisting of poloxomers, poloxamines, octoxynol, hydroxylated castor oil, and tyloxapol.

6. The aqueous solution of claim 1 further comprising a tonicity agent.

7. The aqueous solution of claim 6 wherein said tonicity agent is sodium chloride.

8. The aqueous solution of claim 1 further comprising a viscosity modifying agent.

9. The aqueous solution of claim 8 wherein said viscosity modifying agent is selected from the group consisting of lecithin, hydroxymethylcellulose, hydroxypropylcellulose, hydroxypropylmethylcellulose, and methylcellulose, polyvinyl alcohol, and polyvinyl pyrolidone.

* * * * *